United States Patent [19]
Lundbäck

[11] Patent Number: 5,724,966
[45] Date of Patent: Mar. 10, 1998

[54] BIOMEDICAL ELECTRODE

[75] Inventor: Stig Lundbäck, Vaxholm, Sweden

[73] Assignee: Humanteknik AB, Vaxholm, Sweden

[21] Appl. No.: 649,635

[22] PCT Filed: Nov. 16, 1994

[86] PCT No.: PCT/SE94/01082

§ 371 Date: May 14, 1996

§ 102(e) Date: May 14, 1996

[87] PCT Pub. No.: WO95/13743

PCT Pub. Date: May 26, 1995

[30] Foreign Application Priority Data

Nov. 16, 1993 [SE] Sweden ................... 9303788

[51] Int. Cl.$^6$ .................................. A61B 5/04
[52] U.S. Cl. .................. 128/639; 128/640; 128/643
[58] Field of Search .......................... 128/639–644; 607/152

[56] References Cited

U.S. PATENT DOCUMENTS

| | | | |
|---|---|---|---|
| 4,369,793 | 1/1983 | Staver et al. | 128/643 |
| 4,646,747 | 3/1987 | Lundback | 128/643 |
| 4,708,381 | 11/1987 | Lundback | 294/64.1 |
| 4,736,749 | 4/1988 | Lundback | 128/643 |
| 4,938,218 | 7/1990 | Goodman et al. | 128/643 |
| 5,345,935 | 9/1994 | Hirsch et al. | 128/642 |

FOREIGN PATENT DOCUMENTS

WO 93/16633  9/1993  WIPO .

*Primary Examiner*—Jennifer Bahr
*Assistant Examiner*—David Ruddy
*Attorney, Agent, or Firm*—Hill, Steadman & Simpson

[57] ABSTRACT

An absorber assembly for use in a biomedical electrode, such as an ECG electrode, comprises a contaminant absorber and a support which is combined with the contaminant absorber to form an assembly. The support has a recess for receiving an electrode member. An electrically insulating portion of the support is provided between the electrode member recess and the contaminant absorber. The contaminant absorber also has a capillary break with respect to the electrode member recess. The absorber assembly may include the electrode member.

9 Claims, 2 Drawing Sheets

BIOMEDICAL ELECTRODE

BACKGROUND OF THE INVENTION

This invention relates to biomedical electrodes, that is, electrodes for use in carrying out examinations or treatments in which an electrode is kept in electrical contact with the skin of a patient. ECG and EEC electrodes are examples of electrodes of that kind.

More particularly, the invention relates to absorber means for use in an electrode of the aforementioned kind and serving to absorb moist contaminants, such as sweat, electrolytic gel, saline or the like, from the skin area adjacent the electrode.

An electrode of the aforementioned kind is incorporated in the vacuum electrode device disclosed in WO93/16633. It comprises a contaminant absorber which is combined with a support that also serves as a sealing member and with an electrode member to form a readily replaceable unit.

The contaminant absorber serves to prevent moist contaminants, such as sweat or other skin secretions from the area of the skin where the electrode is applied, or agents applied to the skin or the electrode member to improve the electrical contact between the skin and the electrode member, from contacting and contaminating that part of the electrode device which holds the electrode member in position on the skin and which is not frequently replaced; normally, the unit in which the contaminant absorber is incorporated is replaced after each use or after a few uses.

However, the contaminants are problematic not only because they soil the electrode components they come into contact with. It has been found that they often have an adverse and unpredictable effect on the signals taken up from the patient through the electrode member, e.g. in ECG measurements.

It is not clear why the contaminants have this adverse effect, but the explanation is believed to be that they result in the electrode member being in electrical contact with the skin not only over the well-defined skin area which the skin engaging face of the electrode member contacts, but also over an undefined surrounding skin area; the connection between the last-mentioned area is by way of a surface layer of contaminant fluid which possesses a varying conductivity.

It has been found that the contaminant absorber efficiently takes up the contaminants around the skin engaging face of the electrode member. However, although the absorber when dry is a good electrical insulator, the absorption of the contaminants confers a certain electrical conductivity on the absorber. Because a portion of the absorber of the prior art electrode contacts the electrode member, there is a possibility for the contaminants absorbed into the absorber to establish an electrical connection between the electrode member and the skin area surrounding it.

Regardless of what actually causes the problem, the construction according to the present invention as set forth in the claims greatly reduces it.

SUMMARY OF THE INVENTION

As will become apparent from the following description, the solution comprises mounting the contaminant absorber on a support such that it will be electrically insulated from the electrode member even when the contaminant absorber has taken up contaminants. Preferably, the arrangement is such that there will also be a capillary break or interruption between the contaminant absorber and the electrode member, that is to say that there will be no path on which the contaminant can migrate under capillary action up to the electrode member.

The assembly formed by the contaminant absorber and the support may optionally include the electrode member; if desired, the latter may be provided separately and combined with the absorber-support assembly when the assembly is to be used.

If the electrode member is not a permanent part of the absorber-support assembly, it may be combined with it by attaching, by means of a snap-action connector or the like, the absorber-support assembly to the rest of the electrode device, on which the electrode element is mounted.

Alternatively, the absorber-support assembly may first be combined with the electrode member whereupon the unit so formed can be attached to the rest of the electrode device.

When the absorber-support assembly is intended for use in a vacuum electrode device, the support advantageously can also form the sealing member which serves to define a vacuum compartment around the skin-engaging portion of the electrode member, or a portion of this sealing member.

An embodiment of the invention will be described in greater detail below with reference to the accompanying drawings which show a vacuum electrode device embodying the invention.

DETAILED DESCRIPTION OF THE PREFERRED EMBODIMENT

Figure 1:
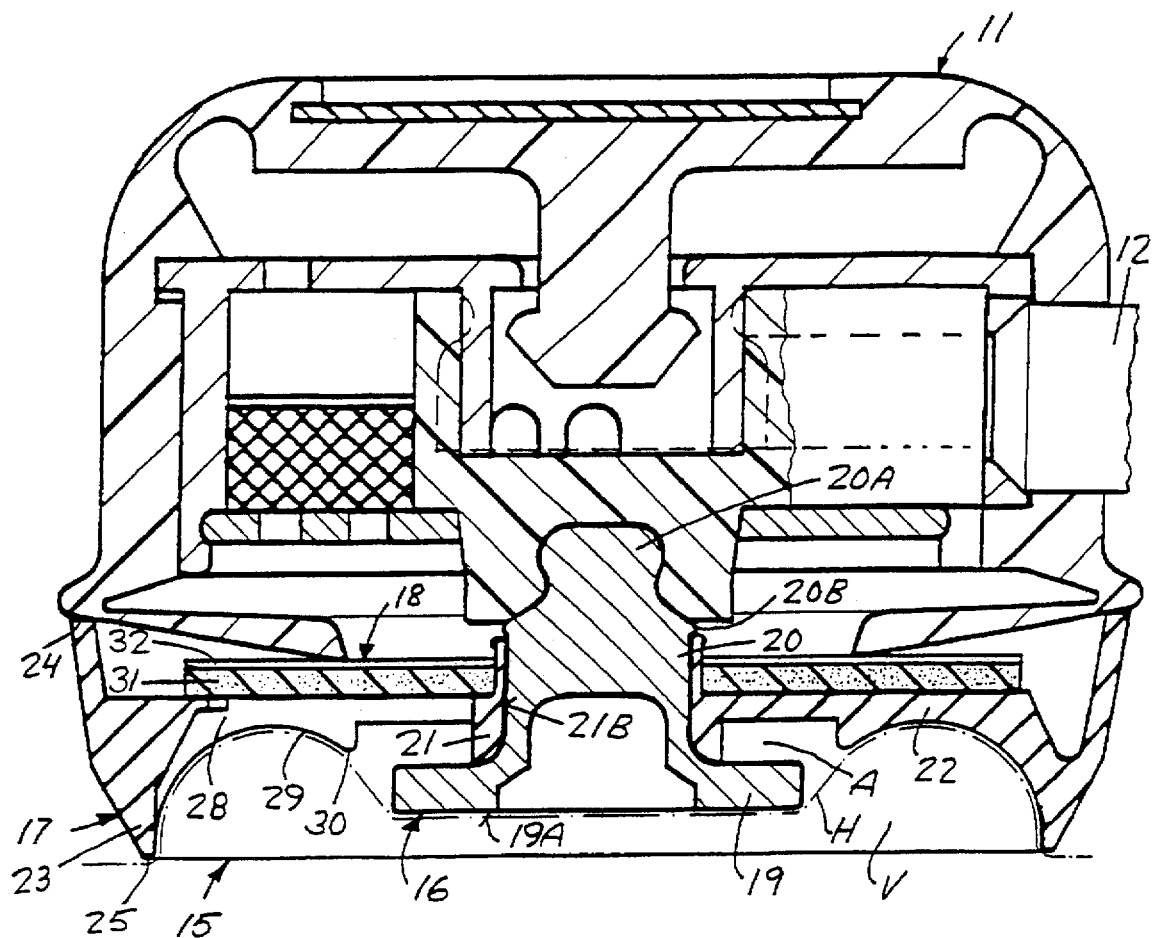
FIG. 1 is a central vertical sectional view of the vacuum electrode device.

The vacuum electrode device shown in FIG. 1 is intended for use in ECG measurements and comprises two main parts. One of these main parts is an electrode holder or head, generally designated by 11, which is adapted to be connected through a wire and hose assembly 12 to an ECG apparatus (not shown) which comprises circuitry for processing and recording electric signals taken up by means of the electrode device, and also a vacuum and pressure pump. The other main part is an electrode unit, generally designated by 15, which is attached to the electrode holder in a manner that permits it to be readily detached from it.

Electrode holder 11 is constructed substantially as illustrated and described in WO93/16633 (FIGS. 7–9). As the detailed construction of the electrode holder 11 does not form part of the present invention, it will not be described in detail here. Instead, for a detailed description of the construction and operation of the electrode holder 11, reference is made to the just-mentioned publication, which is incorporated in the present disclosure by reference.

In the embodiment illustrated in the drawings, the electrode unit 15 is made up of three parts which are detachably interconnected: an electrode member 16, a sealing member 17 and a contaminant absorber 18. These two parts, the contaminant absorber 18 and the sealing member 17, which serves as a support or mount for the contaminant absorber 18, form an independent subunit or subassembly (shown in FIG. 2) of the electrode unit.

Electrode member 16, which may be made of plastic and provided with an electrically conductive surface coating, comprises a lower portion forming a disk-like skin engaging or contacting portion 19 the underside 19A of which is adapted in use of the electrode device to engage the skin of a patient, and a shank 20 which extends upwardly from the upper side of the skin engaging portion and terminates in a contact head 20A by means of which the electrode member 16 and, consequently, the entire electrode unit 15 is attached to the electrode holder 11.

Sealing member 17 is integrally made from a polymer material, for example, or from some other suitable nonconducting material and comprises: a centre or hub portion 21 which forms a socket or recess 21A for the electrode member 16 and is slid over the shank 20 thereof, a perforate support base 22 having a flat upper side and extending transversely of the axis of the hub portion, and an annular sealing lip 23 which extends around the periphery of the support base to define a vacuum compartment between the electrode holder 11 and the skin of the patient. The sealing member 17 is adapted to engage the skin of the patient by its annular lower edge 25 and to engage the underside of the electrode holder 11 by its annular upper edge 24. The support base 22 forms a seat which receives the contaminant absorber 18 and holds it in position on the sealing member.

A tubular collar portion 26 of the hub portion 21 extends downwardly from the support base 22, and its lower edge engages the upper side of the skin engaging portion 19 of the electrode member 16 such that an air gap A exists between the underside of the support base 22 and the upper side of that area of the skin contact portion which projects laterally beyond the hub portion 21. Suitably, the height of this air gap A may be about 1 mm.

Moreover, the hub portion 21 comprises a tubular neck 27 which extends upwardly from the support base 22 and the upper end of which is positioned immediately below a small annular bead 20B on the shank 20 of the electrode member 16. Accordingly, there is a snap-lock attachment of the electrode member 16 to the sealing member 17 such that these two parts of the electrode unit 15 can readily be interconnected and separated and, when interconnected, are reliably held together in a well-defined position relative to one another, see FIG. 2.

Figure 3:
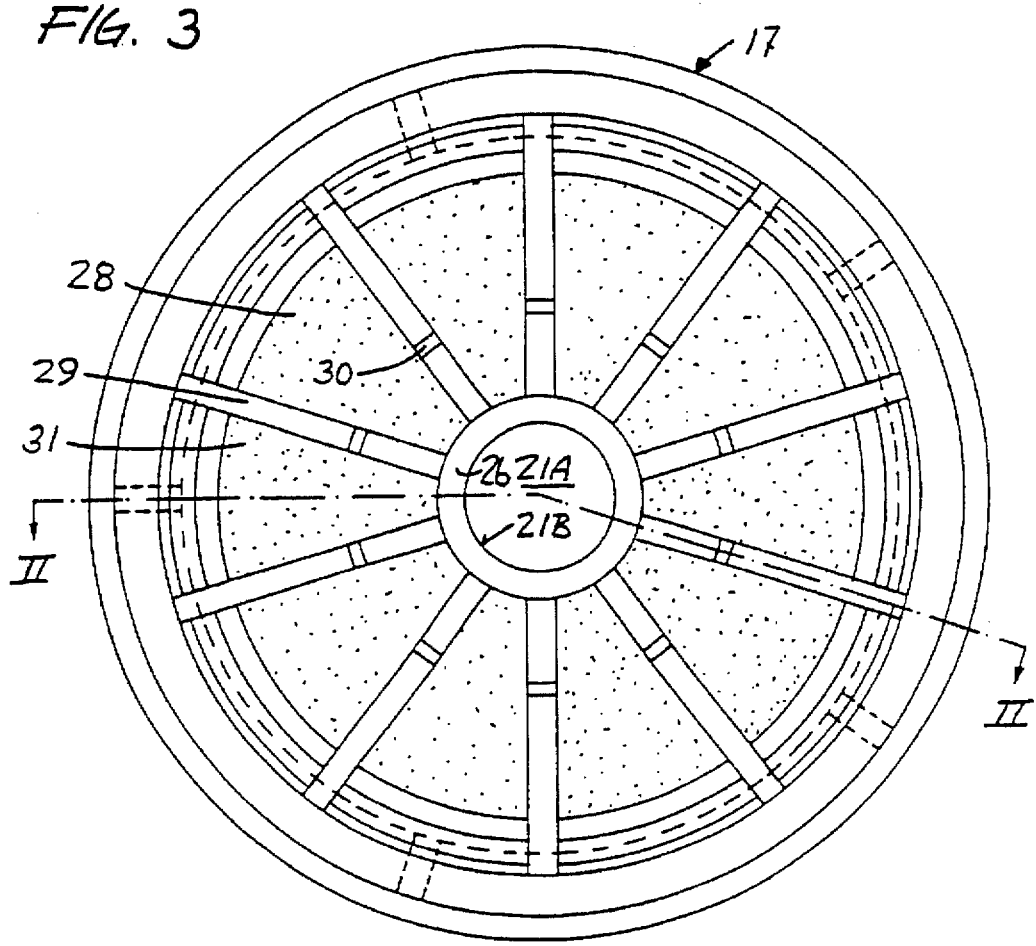
FIG. 3 is a bottom plan view of the assembly shown in FIG. 2.

The support base 22 of the sealing member 17 may be perforated in various ways and may comprise, for example, a number of small holes or, as in the illustrated embodiment, a number of openings 28 in the shape of sectors of a circle which extend over all, or the major portion, of the area between the hub portion 21 and the sealing lip 23 and are separated by radial lands or "spokes" 29. One such opening 28 is shown to the left of the hub portion 21 in FIGS. 1 and 3, see also FIG. 3. The design of the perforation is not critical but should allow the contaminant absorber 18 to act at the skin through the perforation in order to absorb contaminants from the skin as directly and efficiently as possible.

At the upper end of the neck 17 on the hub portion 21 of the sealing member 17 a small external annular bead 27A is provided which ensures a snap-action attachment of the contaminant absorber 18 to the sealing member 17 as will be described below.

Figure 2:
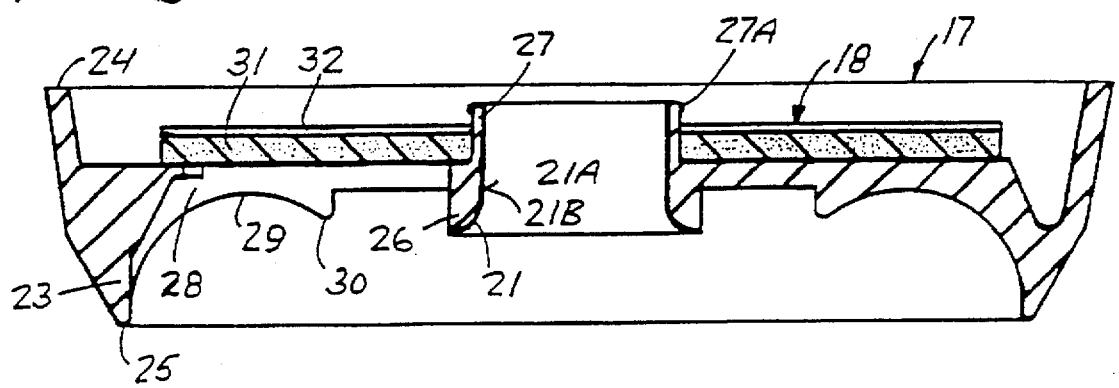
FIG. 2 is a sectional view on line II—II of FIG. 3 and shows the assembly formed by the contaminant absorber and the support therefor, which assembly is part of the vacuum electrode device of FIG. 1.
Figure 2A:
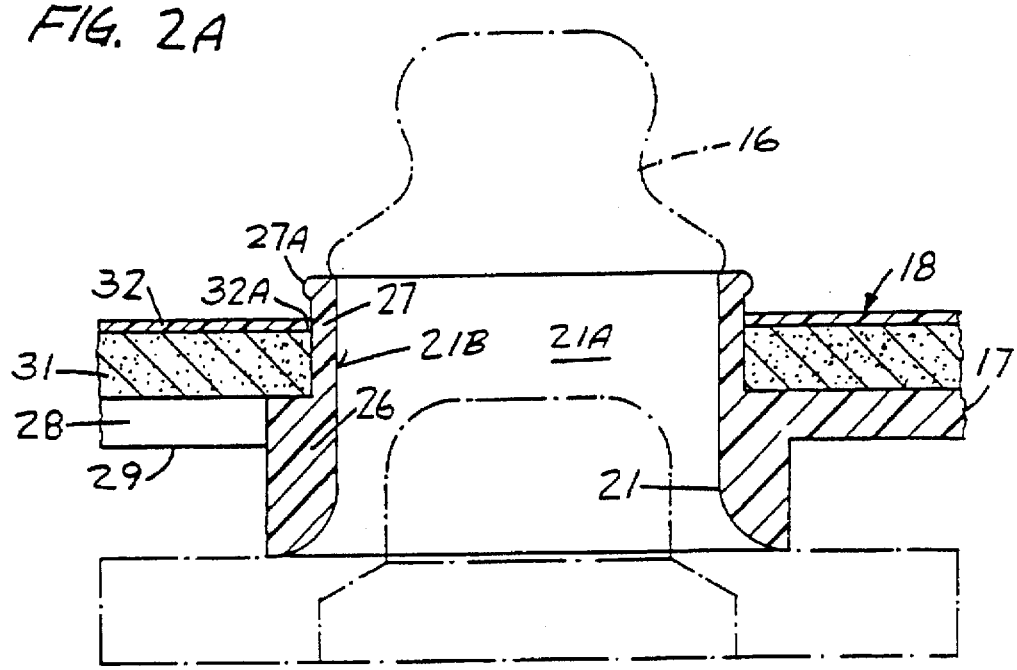
FIG. 2A is an enlarged sectional view of the central portion of the absorber-support assembly of FIG. 2 with the electrode member shown in phantom lines.

When viewed in cross-section as in FIGS. 1 and 2, the undersides of the above-mentioned lands 29 have an upwardly curved contour which extends from the lower edge 25 of the sealing lip 23 and radially inwardly and upwardly to a projection 30 the downwardly directed apex of which is situated slightly higher than, and radially outwardly of, the skin engaging portion 19 of the electrode member 16. When the electrode device is applied to the skin and held to it by vacuum, the lands thereby form a support surface and hold-down element to prevent the vacuum in the vacuum compartment V from pulling up the skin around the side of the skin engaging portion 19 and to stabilize the skin and prevent it from coming into engagement with the circumferential side wall of the skin engaging portion 19. This reduces the possibility of undesired and uncontrolled impedance variations and improves the patient comfort.

Contaminant absorber 18 is positioned on the upper side of the support base 22 of the sealing member 17. In the illustrated embodiment the contaminant absorber comprises a circular disk 31 of a material with high capability of absorbing and retaining moisture, preferably a so-called super absorbent material, and a cover disk 32 which is substantially congruent with the absorber disk and impermeable at least to moisture (some permeability to air can be accepted). In the illustrated embodiment the cover disk 32 is a separate thin disk of plastic, waxed paper or the like which covers the absorber disk 31, but it my also be integrated with the absorber disk 31 and produced by spreading or otherwise applying a sealing composition on the absorber disk, for example.

Both the absorber disk 31 and the cover disk 32 have a central aperture of approximately the same diameter as the neck 27 of the sealing member. Together with the aperture region 32A of the relatively rigid cover disk 32, the bead 27A of the neck 27 forms a snap-lock connector which retains the contaminant absorber 18 on the sealing member 17 and at the same time the neck 27 centres the contaminant absorber on the sealing member.

Sealing member 17 is made of an electrically insulating material. It therefore functions as an electrical insulation between, on the one hand, the contaminant absorber 18 and, on the other hand, the electrode member 16 or the circumferential interior surface 21B which defines the recess 21A of the sealing member 17 and which in use contacts the electrode member. Consequently, the contaminant absorber 18 cannot pass current between the electrode member 16 and the skin area around the skin engaging portion 19 of the electrode member; in FIG. 1 the skin is indicated by a phantom line H. At the same time, the contaminant absorber 18 ensures that the skin area adjoining the skin engaging portion 19 is kept free from a layer of contaminants, such a sweat, which might function as a conductor of electric current.

An important feature of the invention is that the possibility of capillary transport of moisture from the skin or from the contaminant absorber 18 to the electrode member 16 is eliminated by the construction of the support and absorber assembly 17–18 or the electrode unit 15 according to the invention. Contributive to this in the assembly according to the invention is the air gap A which acts as a capillary break or interruption and thereby prevents capillary migration of moisture along the passage between the upper side of the skin engaging portion 19 of the electrode member 16 and the underside of the support base 22 of the sealing member 17. The underside of the lands 29 and the projections 30 prevent the skin from being drawn inwardly far enough to eliminate the capillary break or interruption.

As is apparent from the drawing, there is also no possibility of moisture migrating under capillary action from the absorber 18 and in between the electrode member shank 20 and the collar 26 or the neck 27 of the sealing member. Moisture can migrate through the absorber 18 as far as up to the hub portion 21 of the sealing member 17, but the hub portion 21 provides an electrical insulation between the absorber 18 and the electrode member 16 or the circumferential surface 21B, and the outer circumferential surfaces of the collar 26 and the neck 27 form anti-capillary or capillary-breaking surfaces by being exposed to the air over a substantial height so that they effectively prevent migration of moisture downwardly and upwardly from the absorber 18. This prevention of migration of moisture is enhanced by the material of the sealing member 17 being hydrophobic.

Thus, the electrode member 16 has both electrical insulation and capillary break or interruption with respect to the contaminant absorber 18 and the areas of the skin which in use come into electrically conducting contact with the absorber.

With the construction according to the invention the skin surface with which the electrode member is conductively engaged will be well-defined.

The usefulness of the electrode unit or absorbent and support assembly is not restricted to vacuum electrode devices, that is, electrode devices which are held to the skin (or some other surface to which the electrode is applied) by the action of a pressure differential between the outer or upper side of the electrode holder and a vacuum compartment defined at the inner side of the electrode holder. For example, the electrode unit or absorbent-support assembly can be used with other types of electrode devices, such as electrode devices which are adhesively attached to or held in position on the skin by clips or straps or the like.

When used with other or non-vacuum types of electrode devices, the element which serves as the support for the contaminant absorber, and which in the drawings is represented by the sealing member 17, need not have any sealing function. Accordingly, it is within the scope of the invention to employ as the support for the contaminant absorber parts which serve exclusively or chiefly as a support for the contaminant absorber.

As pointed out above, before use of the electrode device, the electrode element need not be a part of the assembly which consists of the contaminant absorber and its support. Limitation of this assembly to the contaminant absorber and its support often is advantageous because the assembly can then be stacked in a more space-saving manner than would be possible if the electrode member were also included. If the electrode member is not included in the absorber-support assembly, it may be attached to the rest of the electrode device (the electrode holder 11 in the illustrated embodiment) and it may then be constructed such that it can be readily cleaned and need not be replaced after each use.

What is claimed is:

1. An absorber assembly for use in a biomedical electrode, comprising:

an electrically insulative support member having a disk shaped configuration with a forward major surface, an opposed rearward major surface and a projecting central hub portion extending from a first end spaced from the forward major surface to a second end spaced from the rearward major surface and having a central aperture extending therethrough and defining an electrode receiving space; and a contaminant absorber disposed on the rearward major surface adjacent the second end of the hub portion.

2. An absorber assembly as defined in claim 1, wherein the first end of the hub portion is effective to maintain an electrode inserted into said electrode-receiving space in a spaced apart relation from said forward major surface to define a capillary break therebetween.

3. An absorber assembly as defined in claim 1, wherein said support member comprises a hydrophobic material.

4. An absorber assembly as defined in claim 1, wherein the contaminant absorber is held to the support member by a pair of positively interlocking members.

5. An absorber assembly as defined in claim 1, wherein the contaminant absorber has a layered structure including a layer of moisture absorbing material disposed on the rearward major surface and a fluid-tight layer disposed on the moisture absorbing material layer.

6. An absorber assembly as defined in claim 1, wherein the support member includes a plurality of apertures extending therethrough.

7. An absorber assembly as defined in claim 1, wherein the support member further includes skin hold down members projecting from said forward major surface.

8. An absorber assembly as defined in claim 1, wherein the support member further includes a peripheral sealing lip on the forward major surface adapted to engage a patient's skin to define a vacuum compartment.

9. An absorber assembly as defined in claim 1, further comprising an electrode member disposed in the electrode receiving space of the support member.

* * * * *